US009662471B2

(12) United States Patent
Coppi

(10) Patent No.: US 9,662,471 B2
(45) Date of Patent: May 30, 2017

(54) CONTROLLED DEFORMATION CATHETERS

(71) Applicant: Gioachino Coppi, Modena (IT)

(72) Inventor: Gioachino Coppi, Modena (IT)

(*) Notice: Subject to any disclaimer, the term of this patent is extended or adjusted under 35 U.S.C. 154(b) by 121 days.

(21) Appl. No.: 14/780,601

(22) PCT Filed: Jan. 24, 2014

(86) PCT No.: PCT/IB2014/058516
§ 371 (c)(1),
(2) Date: Sep. 28, 2015

(87) PCT Pub. No.: WO2014/155210
PCT Pub. Date: Oct. 2, 2014

(65) Prior Publication Data
US 2016/0030711 A1  Feb. 4, 2016

(30) Foreign Application Priority Data
Mar. 29, 2013 (IT) .............................. PD2013A0081

(51) Int. Cl.
A61M 25/00  (2006.01)

(52) U.S. Cl.
CPC .... A61M 25/0052 (2013.01); A61M 25/0051 (2013.01)

(58) Field of Classification Search
CPC ......... A61M 25/0051; A61M 25/0052; A61M 25/005; A61M 25/0053; A61M 25/0043; A61M 25/0054; A61M 25/00; A61M 25/0023
USPC ....................................................... 604/526
See application file for complete search history.

(56) References Cited

U.S. PATENT DOCUMENTS

| 2004/0034343 A1* | 2/2004 | Gillespie .......... A61B 17/00234 606/15 |
| 2008/0188928 A1* | 8/2008 | Salahieh ........... A61M 25/0054 623/2.11 |
| 2010/0082000 A1* | 4/2010 | Honeck ............. A61M 25/0045 604/246 |

FOREIGN PATENT DOCUMENTS

| WO | 9315784 A1 | 8/1993 | |
| WO | WO 9315784 A1 * | 8/1993 | ........ A61M 25/0012 |

* cited by examiner

Primary Examiner — Jason Flick
(74) Attorney, Agent, or Firm — Robert E. Alderson, Jr.

(57) ABSTRACT

Catheters are provided which have a high capacity of axial (pushability) and rotational (torquability) movement with relative maximum flexibility and which, at the same time have the ability to adapt to at least partial variations of diameter under the thrust of other catheters or dilators travelling though the lumen or so as to flatten itself at least partially to travel through the lumen of other catheters, such as for example feed catheters.

22 Claims, 10 Drawing Sheets

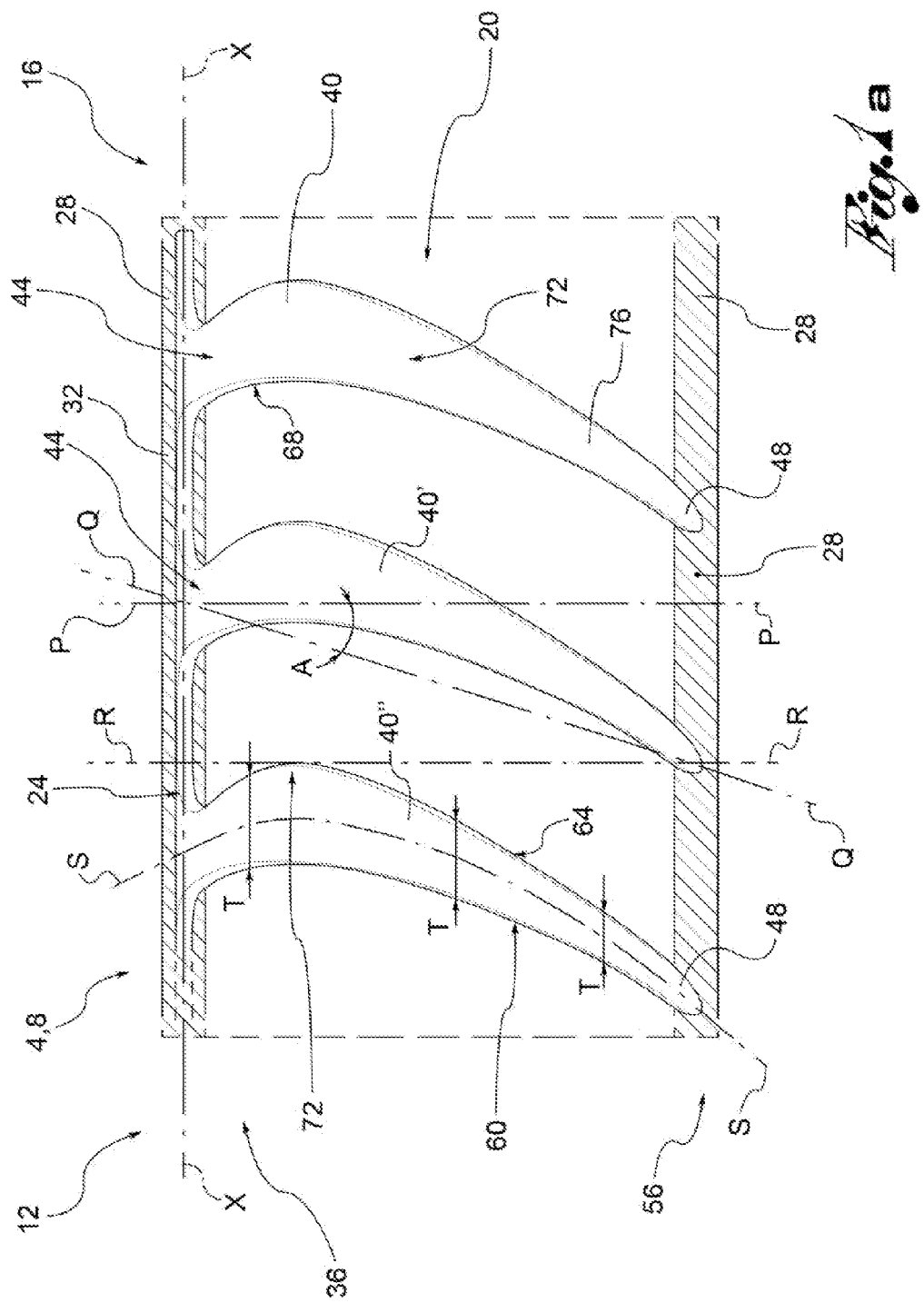

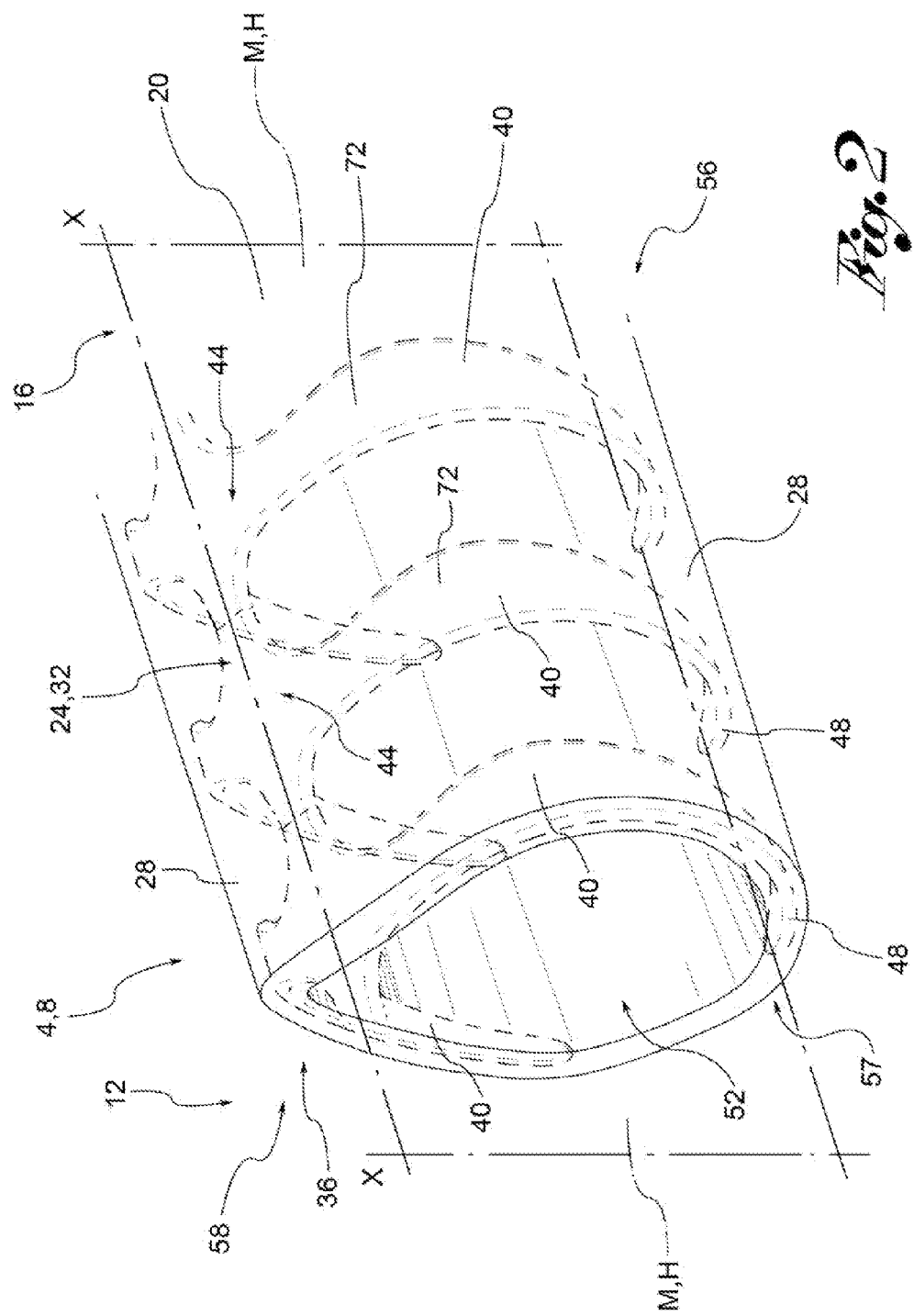

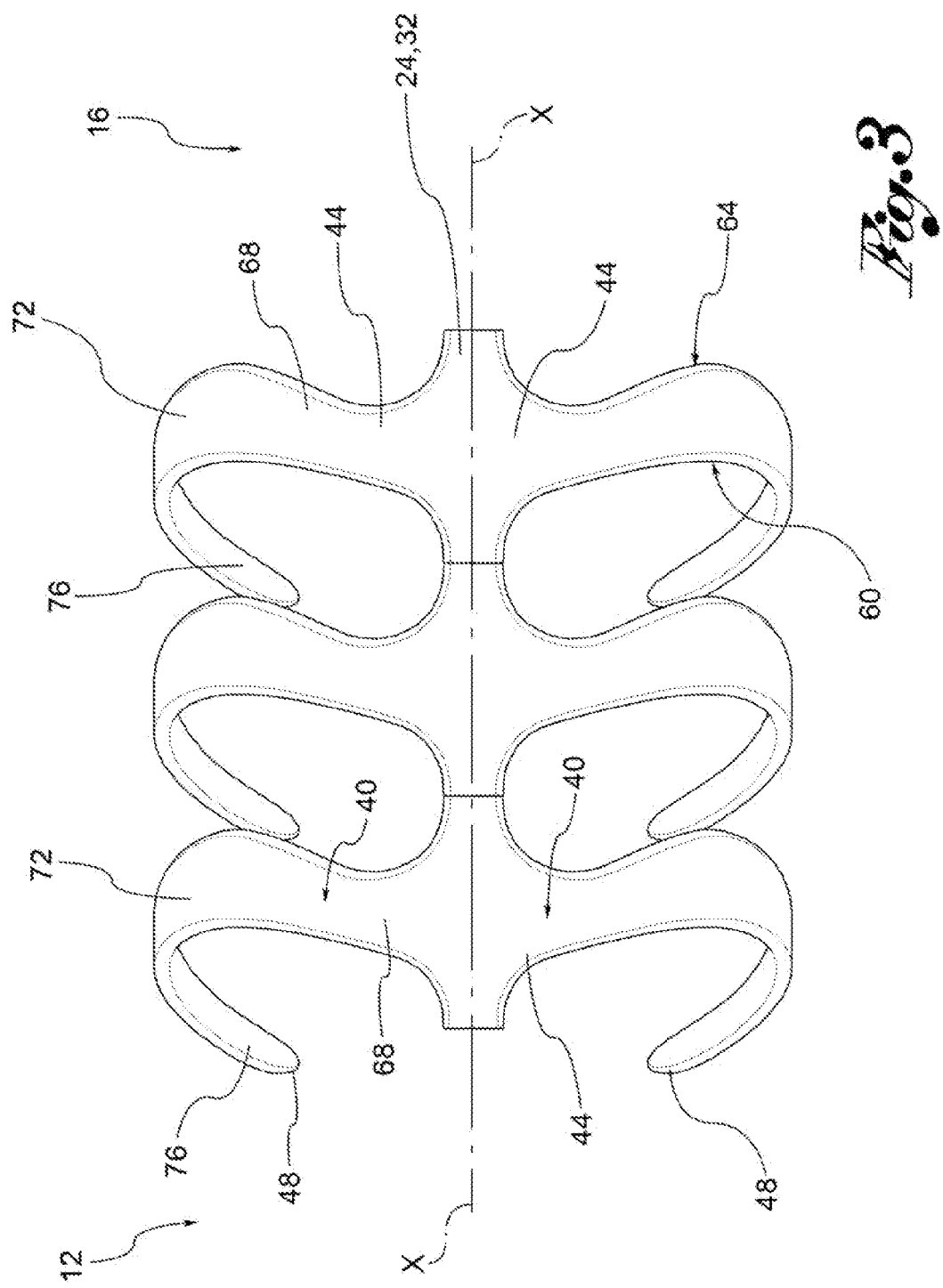

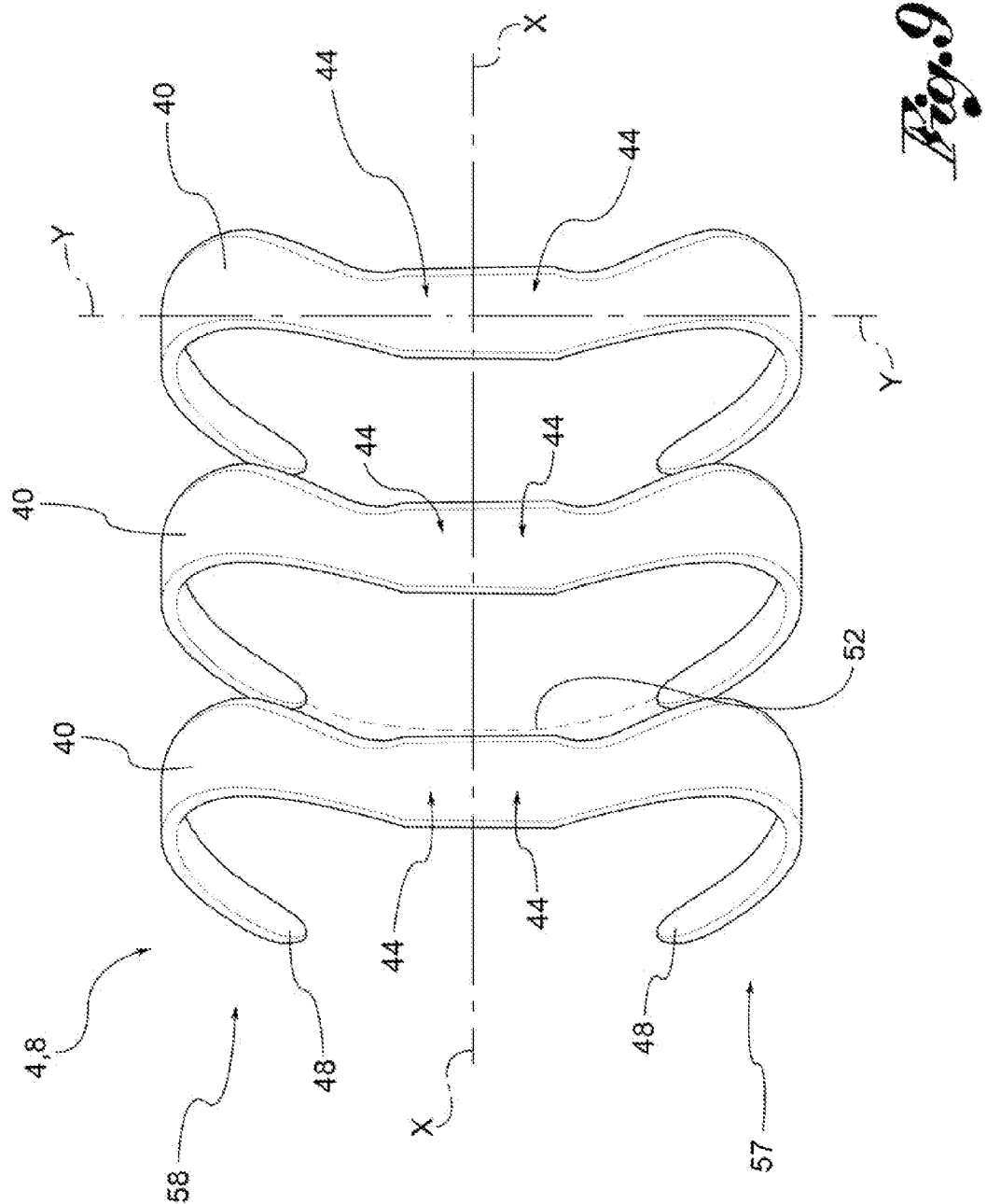

CONTROLLED DEFORMATION CATHETERS

CROSS-REFERENCE TO RELATED APPLICATIONS

This application is a National Phase Application of PCT International Application No. PCT/IB2014/058516, International Filing Date, Jan. 24, 2014, claiming priority to Italian Patent Application No. PD2013A000081 (102013902142496), filed Mar. 29, 2013 each of which is hereby incorporated by reference in its entirety.

FIELD OF THE INVENTION

The present invention relates to a controlled deformation catheter and in particular to a catheter suitable to modify the cross section of the inner lumen both so as to permit the passage of other catheters, dilators and/or instruments of various types therein, and so as to permit its deformation for the insertion of another catheter, such as for example, a guide catheter.

BACKGROUND OF THE INVENTION

The catheters used in the human body, in particular vascular catheters for angioplasty and stenting need support to be moved axially (pushability) and to rotate (torquability) as well as requiring flexibility to move up the arterial tree and the veins for this reason catheters are usually made of a metal core covered in plastic material.

The current standard core of catheters is composed of a mesh lamina or, to give maximum flexibility, of a coil core. In both cases the catheter has a predefined diameter with no possibility of adaptability to possible, even minimal, variations of diameter required.

This impossibility of adapting in shape in practice constitutes a significant limitation to the applications of said catheter.

SUMMARY OF THE INVENTION

The purpose of the present invention is to make a catheter which retains a high capacity of axial (pushability) and rotational (torquability) movement with relative maximum flexibility and which, at the same time has the ability to adapt to at least partial variations of diameter under the thrust of other catheters or dilators travelling though the lumen or so as to flatten itself at least partially to travel through the lumen of other catheters, such as for example feed catheters.

Such purposes are achieved by catheters as described and claimed herein.

Further characteristics and advantages of the present invention will be more clearly comprehensible from the following description, given purely by way of non-limiting examples with reference to the attached drawings.

BRIEF DESCRIPTION OF THE FIGURES

FIG. 1a shows a side view of a catheter according to one embodiment of the present invention, in a non-deformed configuration;

FIG. 2 shows a perspective view of a catheter according to the present invention, in a non-deformed configuration;

FIG. 3 shows a perspective view in a deformed configuration, of the catheter in FIG. 2;

FIGS. 8-9 show perspective views of a catheter according to a further embodiment of the present invention.

DETAILED DESCRIPTION

Figure 1B:
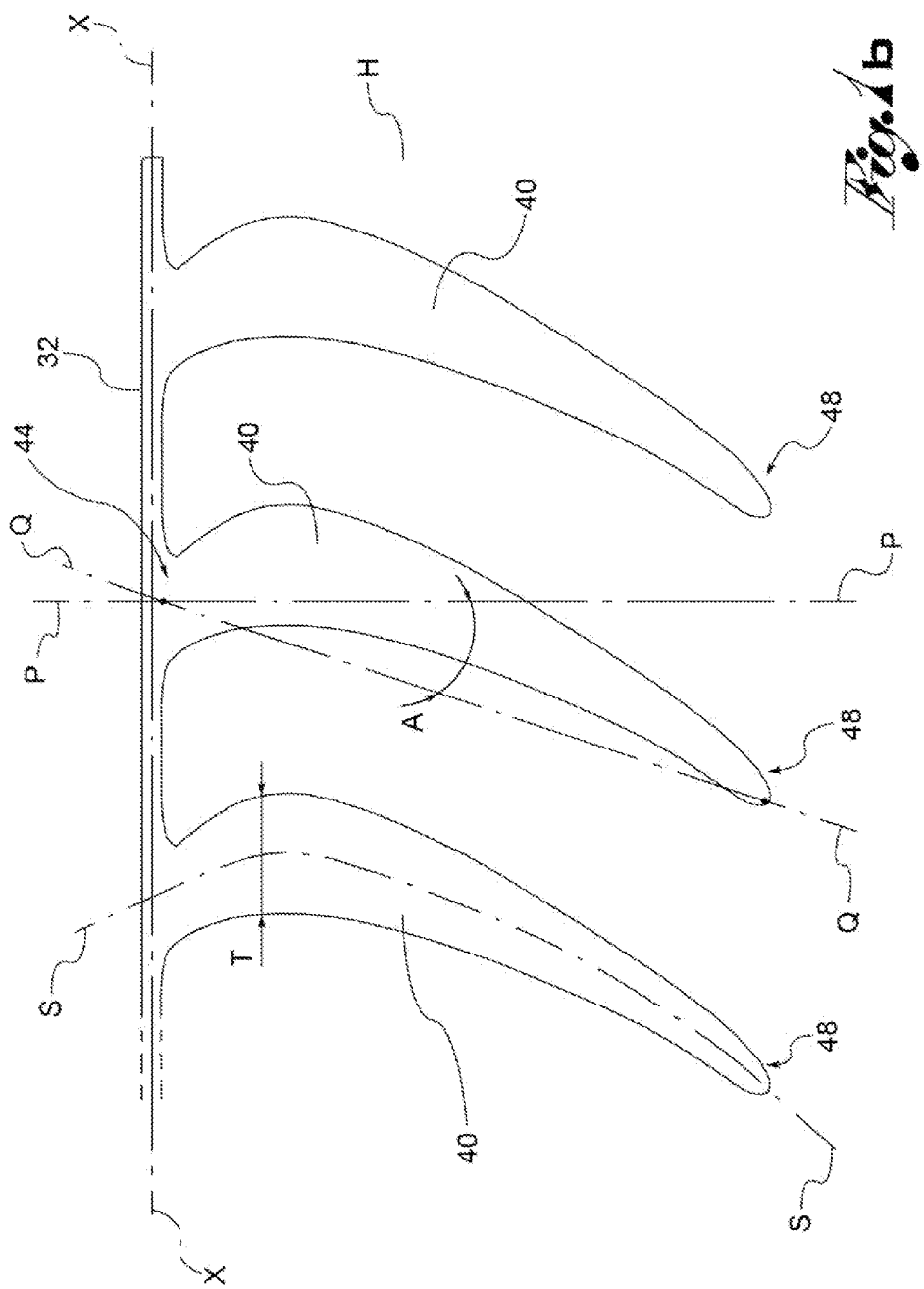
FIG. 1b shows a projection on a centreline plane M of an inner core of the catheter.
Figure 4:
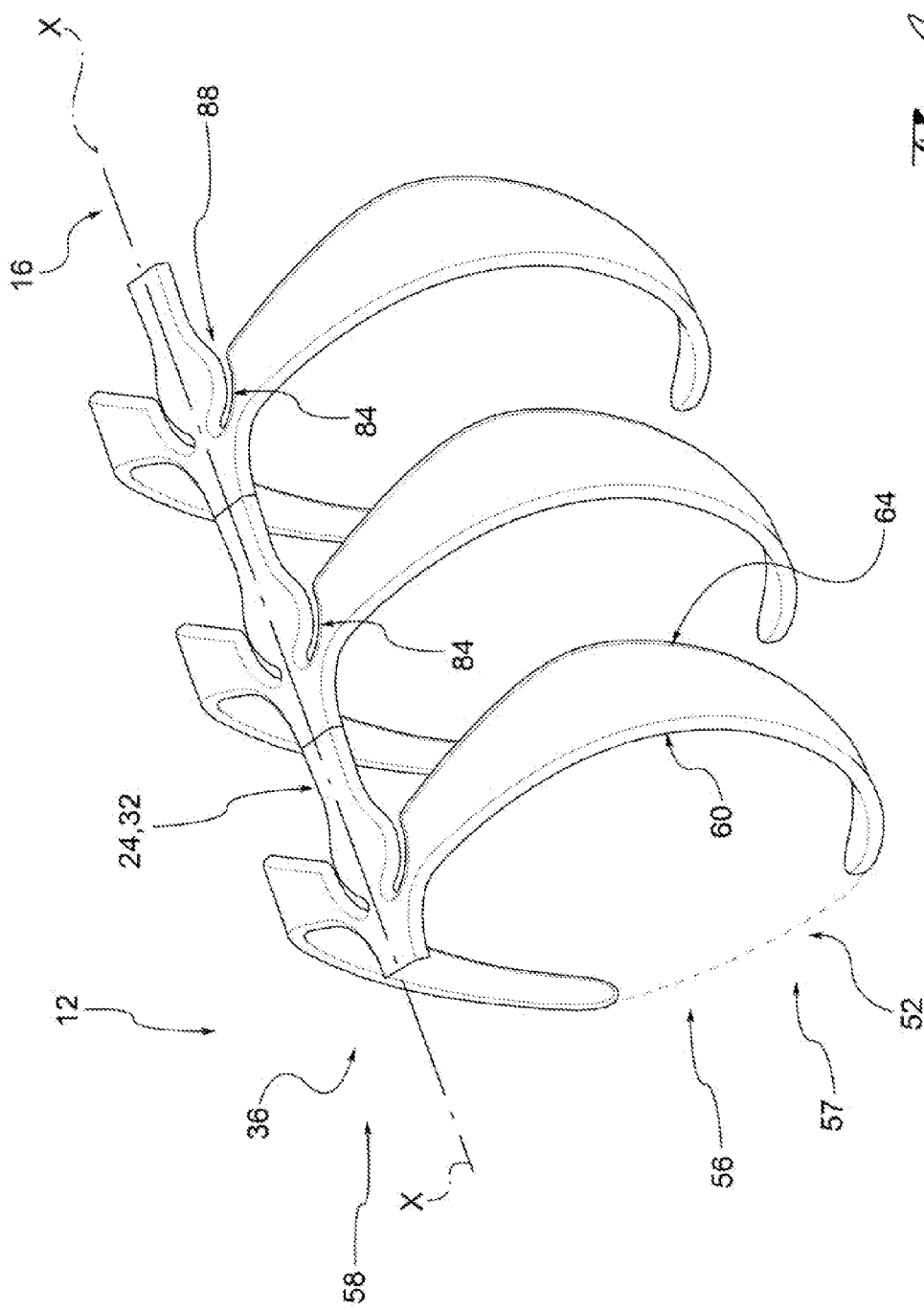
FIG. 4 shows a perspective view of a catheter according to a further embodiment of the present invention.
Figure 5:
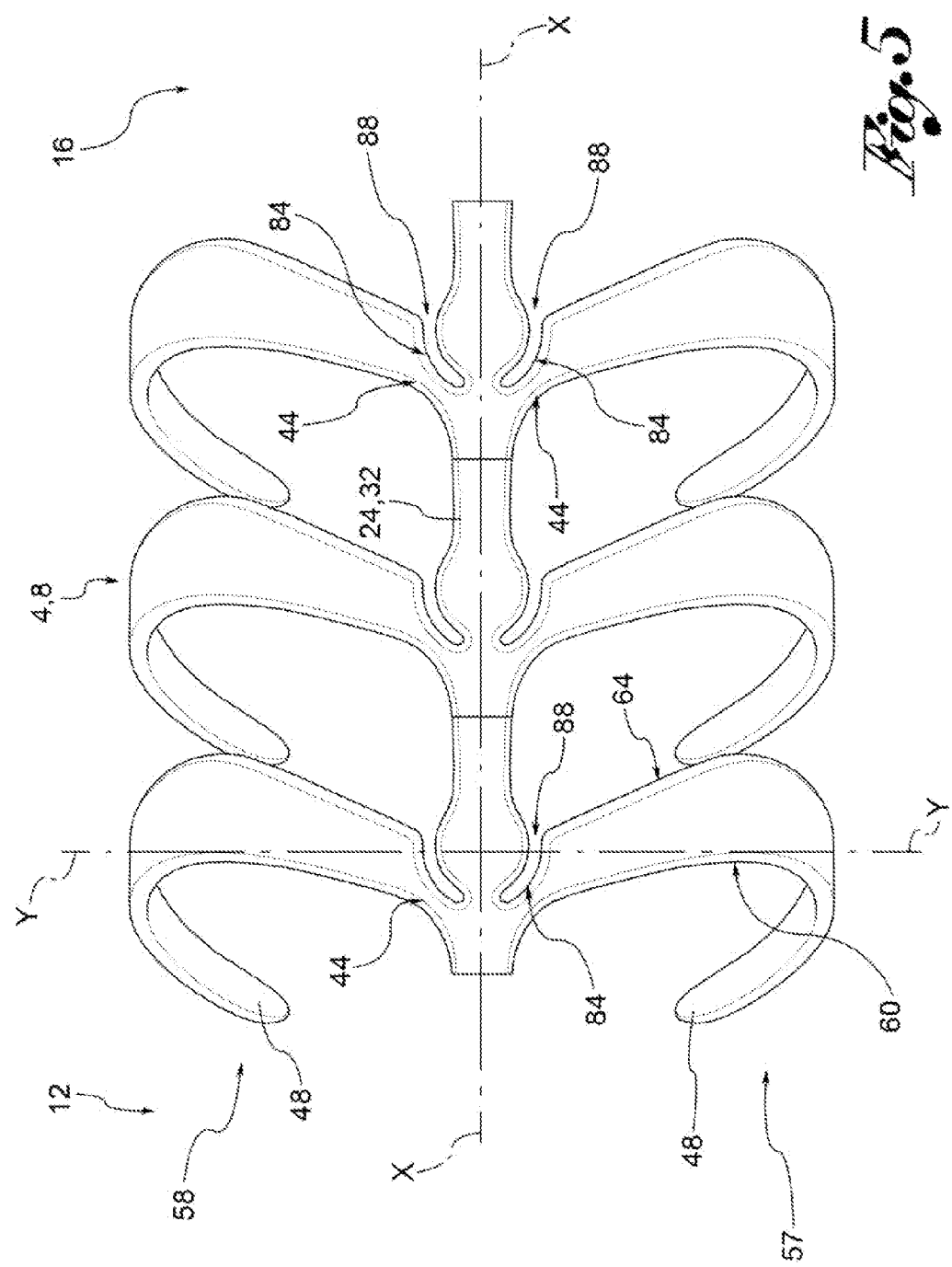
FIGS. 5-7 show perspective views from different angles, in a deformed configuration, of the catheter in FIG. 4.
Figure 6:
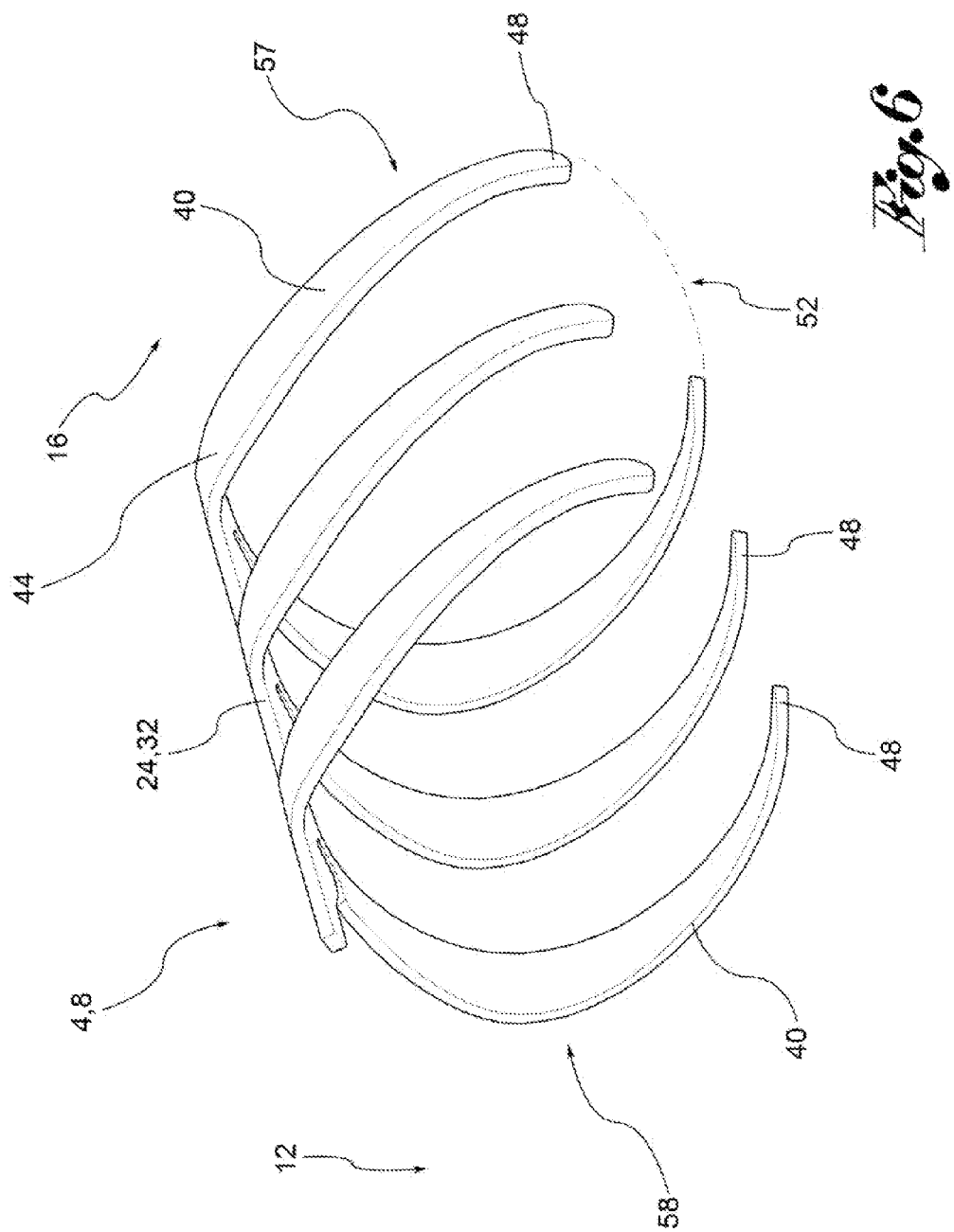
Figure 7:
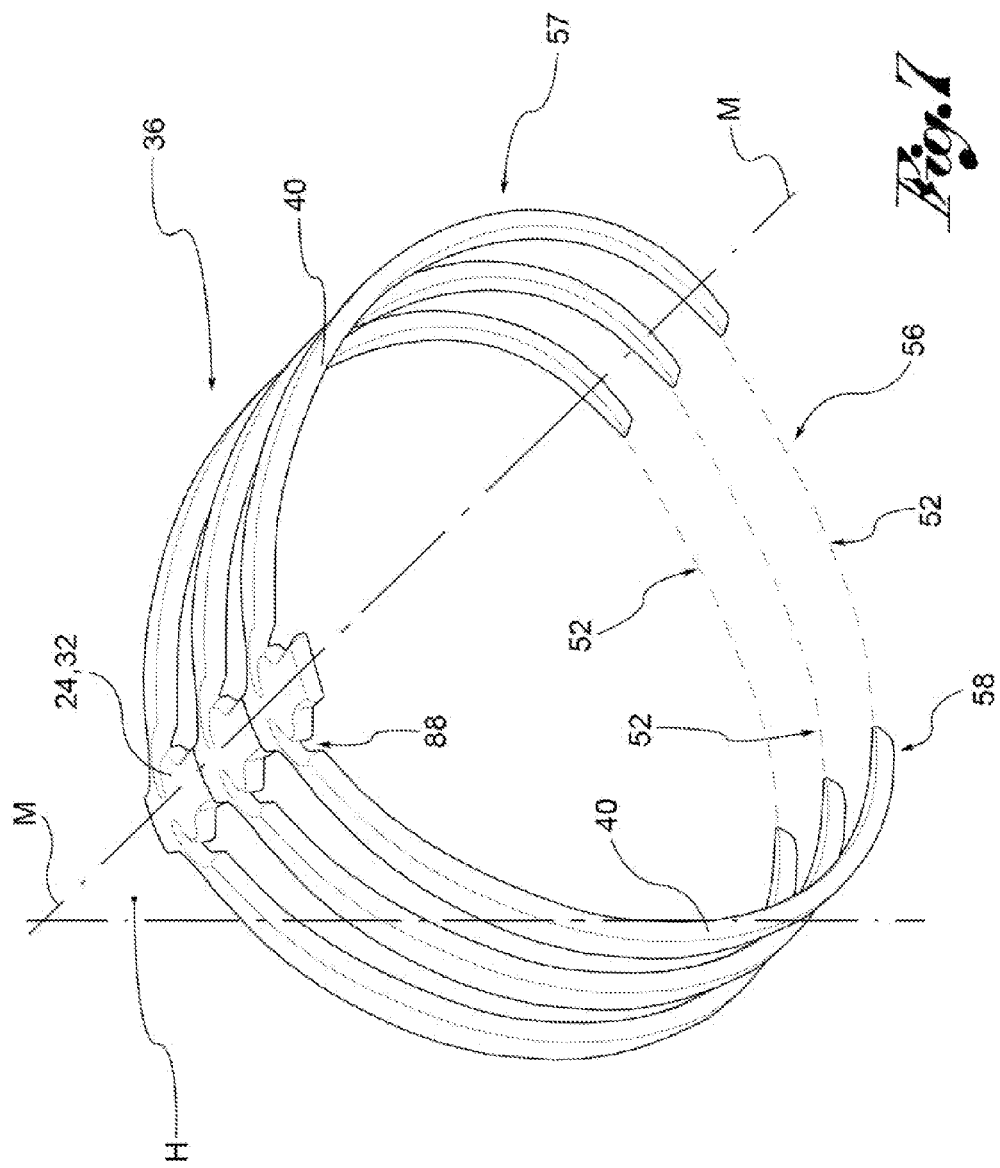
Figure 8:
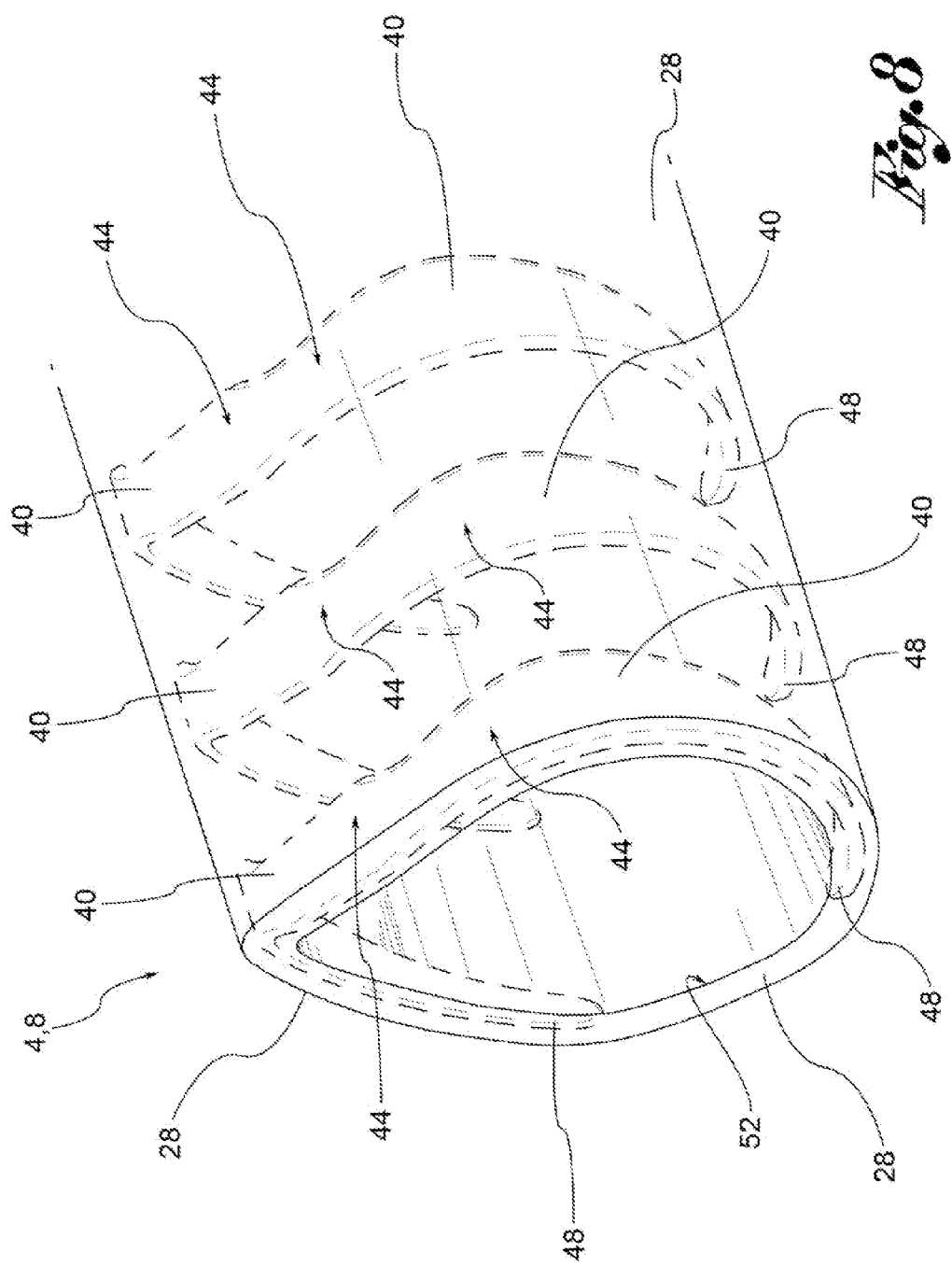

The elements or parts of elements common to the embodiments described below will be indicated using the same reference numerals.

With reference to the aforementioned figures, reference numeral 4 globally denotes a catheter comprising a catheter body 8 which extends from a proximal end 12 to a distal end 16, in a longitudinal direction X-X.

The catheter body 8 is a hollow tubular body which defines at least one lumen 20.

For the purposes of the present invention the catheter body 8 may have varied geometries; for example, the catheter body 8, in relation to a cross-section plane perpendicular to said longitudinal direction X-X, may have a hollow circular cross-section or even a hollow elliptical/oval cross-section.

The cross-section of the catheter body 8, as described further below, also depends on the length and on the inclination of the ribs 40 embedded inside said body.

The catheter body 8 comprises a core 24 embedded inside a flexible, outer covering layer 28. In other words, the outer covering layer 28 has a greater thickness than the thickness of the core 24 so that it is completely covered by said layer. For example, the core is made of nitinol, or in a printed polymer material or in a metal or polymer material obtained by laser printing.

The outer covering layer 28 is preferably made of polymer material.

The covering material, that is the outer covering layer 28 must be sufficiently elastic as to permit the area without the core 24 to extend.

The core 24 comprises a plurality of ribs 40 which extend inside the covering layer 28: said ribs 40 extend from an attachment end 44, at which they connect to each other, to a free end 48, opposite the attachment end 44, wherein the line joining the attachment ends 44 of the pairs of ribs 40 defines a dorsal side 36 of the catheter body 8.

In a rest configuration, as specified further below, said attachment ends 44 are aligned parallel to the longitudinal direction X-X.

According to one embodiment, the core 24 comprises a longitudinal element or backbone 32, defining a dorsal side 36 of the catheter body 8, from which the ribs 40, in pairs, unwind from opposite sides to the longitudinal element 32, extending inside said outer covering layer 28.

The longitudinal element 32 connects the attachment ends 44 of the pairs of ribs 40 to each other.

In other words, the attachment ends 44 of the ribs 40 converge in the longitudinal element or backbone 32 which mechanically connects the pairs of ribs 40 to each other along the longitudinal extension of the catheter body 8.

The free ends 48 of the same pairs of ribs 40 are separate from each other and identify at least one discontinuity 52 of said ribs 40, said discontinuity 52 being positioned on a ventral side 56, opposite said dorsal side 36.

Advantageously, having defined a first plane P perpendicular to the longitudinal element 32 and passing through the attachment end 44 of a rib 40, and having defined a second plane Q passing through the free end 48 and through the attachment end 44 of the same rib 40, said planes P, Q are inclined to each other so as to form an acute angle A on the side of the proximal end 12 or of the distal end 16. In yet other words, the ribs 40 are not perpendicular overall to the longitudinal element 32, but are inclined either backwards, that is towards the proximal end 12, or forwards, that is towards the distal end 16.

The inclinations of the ribs 40 are more clearly visible in FIG. 1*b* which shows the projection of the core of the catheter body 8 on a centreline plane M-M of said catheter body.

For example, the backward inclination of the ribs 40, that is towards the proximal end 12, facilitates the penetration of the catheter 4 in a narrower tube.

These ribs 40 must be inclined co-measuring the inclination, length and aperture depending on whether one wishes to obtain catheters of a circular or oval cross-section. In particular, the inclination favours the deformability and thus the penetrability of the catheter 4 which will also be in relation to the thickness and wideness of said ribs.

For the purposes of the present invention the definition of longitudinal direction and of angular inclinations and orientations of the ribs 40 refer to a rest position wherein the catheter body 8 is positioned in a rectilinear configuration, parallel to said longitudinal direction X-X.

Consequently, the arrangement of the planes, for example first and second P, Q are to be understood as in relation to a rectilinear, rest configuration of the catheter body 8. It is understood that the catheter body 8 is perfectly able to assume any curvilinear configuration so as to follow the winding nature of the vessels; in such curvilinear configuration obviously the inclinations relative to the planes and the ribs 40 may vary depending on the degree of deformation imposed For example the catheter 4 may curve towards the ventral side 56, so as to assume a convex configuration on the dorsal side 36 and concave on the ventral side 56, but also curve towards the dorsal side 36, so as to assume a concave configuration on the dorsal side 36 and convex on the ventral side 56. In addition, the catheter body 8 may also curve in transversal directions Y-Y, perpendicular to the longitudinal direction X-X, so as to assume a concave configuration at a first transversal side 57 and a convex configuration at a second transversal side 58. Obviously the opposite curvature is also possible. The ribs 40 arranged on the transversal side 57,58 which curve in a convex configuration, move away from each other, while the ribs 40 arranged on the opposite transversal side 58,57, which curve in a concave configuration, move towards each other.

In this manoeuvre therefore the curvature of the catheter body is conditioned by the distance between said ribs.

Henceforth in the description, all the geometric configurations described, will always refer to the rectilinear configuration of the catheter body 8.

According to one embodiment, said acute angle A, formed between the first and second plane P, Q, is from 10 to 70 degrees.

According to a further embodiment, said acute angle A, formed between the first and second plane P, Q, is from 40 to 60 degrees.

According to a possible embodiment, the ribs 40, in relation to a projection plane H perpendicular to the longitudinal element 32 and passing through a centreline M of the catheter body 8, have a rectilinear median line S (FIG. 1*b*). The median line S is the place of the midpoints of the longitudinal thicknesses of the ribs 40, said longitudinal thicknesses being measured in relation to lines parallel to said longitudinal direction X-X.

According to a further embodiment, the ribs 40, in relation to a projection plane H perpendicular to the longitudinal element 32 and passing through a centreline M of the catheter body 8, have a curvilinear median line S. As seen, the median line S is the place of the midpoints of the longitudinal thicknesses of the ribs 40, said longitudinal thicknesses being measured in relation to lines parallel to said longitudinal direction X-X.

According to one embodiment, the ribs 40 are curvilinear and are oriented so as to present an intrados 60 or concave portion, on the side of the proximal end 12, and an extrados 64, or convex portion, on the side of the distal end 16.

The inverse configuration is also possible, according to which the ribs 40 are curvilinear and are oriented so as to present an intrados 60 or concave portion, on the side of the distal end 16, and an extrados 64, or convex portion, on the side of the proximal end 12.

According to one embodiment, the ribs 40 present a first section 68 which extends from the attachment end 44 to an intermediate portion 72 and which, in relation to a projection plane H perpendicular to the longitudinal element 32 and passing through a centreline M of the catheter body 8, is inclined towards the distal end 16, and a second section 76 which extends from the intermediate portion 72 to the free end 48 and which, in relation to said projection plane H, is inclined towards the proximal end 12, so that the first and the second sections 68,76 have opposite inclinations to each other.

The inverse configuration is also possible, according to which the first section 68 proves inclined towards the proximal end 12, and the second section 76 proves inclined towards the distal end 16, so that the first and the second sections 68,76 have opposite inclinations to each other.

The fact that the first and the second sections 68, 76 have opposite inclinations to each other improves the behaviour of the ribs 40 during the elastic deformation of the catheter body 8, both on the passage of the catheter body 8 through a lumen of reduced dimensions in relation to the outer diameter of said catheter body, and on the introduction of a body, such as for example an instrument, inside the lumen 20, said instrument having a greater diameter than said lumen.

In fact, the presence of the double curvature counters an excessive closing or widening of the ribs 40 upon the variation in diameter of the catheter body.

Such double curvature of the ribs 40 contributes to the geometric and dimensional control of the catheter body 8.

According to one embodiment, at least an intermediate portion 72 of the ribs 40 extends from the first plane P, passing through the attachment end 44 and perpendicular to the longitudinal element 32, towards the distal end 16 and at least a second section 76 of the rib 40, comprising said free end 48, extends from the first plane P towards the proximal end 12.

According to one embodiment, the ribs 40 are conformed and oriented in such a way that a radial plane R, perpendicular to the longitudinal element, passing through the free ends 48 of a first pair of ribs 40', intercepts at least partially an intermediate portion 72 of a second pair of ribs 40", adjacent to the first pair of ribs 40', on the side of the proximal end 12.

Obviously the inverse configuration is also possible, according to which the ribs 40 are conformed and oriented in such a way that a radial plane R, perpendicular to the longitudinal element, passing through the free ends 48 of a first pair of ribs 40', intercepts at least partially an intermediate portion 72 of a second pair of ribs 40", adjacent to the first pair of ribs 40', on the side of the distal end 16.

According to a possible embodiment, the ribs 40 are thread-shaped, that is obtained from a flexible, thread-shaped filament.

According to a further embodiment, the ribs 40 have a variable axial thickness, said thickness being measured parallel to said longitudinal direction.

According to a further embodiment, said axial thickness of the ribs increases moving from the attachment end 44 towards an intermediate portion 72 and tapers moving from the intermediate portion 72 towards the free end 48, the intermediate portion 72 being comprised between the attachment end 44 and the free end 48.

Preferably, each pair of ribs 40 comprises ribs symmetrical to each other in relation to the longitudinal element 32.

Preferably, the length and curvature of the ribs 40 is modified according to the desired inclination of said ribs.

According to a possible embodiment, the free ends 48 of the same pair of ribs 40 are separate from each other at a discontinuity 52 having a curvilinear extension equal to at least 20% of the total perimeter of the catheter body 8, measured on a cross-section plane perpendicular to said longitudinal element 32.

Preferably, the discontinuity 52 has a curvilinear extension of not more than 50% of the total perimeter of the catheter body 8, measured on a cross-section plane perpendicular to said longitudinal element 32.

According to one embodiment, the ribs 40, at the attachment end 44, comprise at least one notch 84 suitable for favoring the flexing of the ribs 40 towards the proximal end 12, so as to keep a skirt of rib 40 in one piece with the longitudinal element 32, positioned on the attachment end 44 on the side of the proximal end 12 and to have an opening 88 positioned on the attachment end 44 on the side of the distal end 16.

The inverse configuration is also possible, wherein the skirt of rib 40 in one piece with the longitudinal element 32, is positioned on the attachment end 44, on the side of the distal end 16 and the opening 88 is positioned on the attachment end 44 on the side of the proximal end 12.

In general, the notch 84 is positioned on the side opposite to the direction of inclination of the ribs 40; this way if the ribs 40 are inclined towards the proximal end 12, the opening 88 defined by the notch 84 is facing towards the distal end 16, while if the ribs 40 are inclined towards the distal end 16, the opening 88 defined by the notch 84 is facing towards the proximal end 12.

In other words, the notch 84 and the relative opening 88 are positioned so as to facilitate the predefined inclination of the ribs 40.

For example such notch 84 has a circular sector conformation.

Preferably, the opening 88 has an extension of 50% to 80% of the cross-section of solid attachment, in other words the notch consists of a removal of material of 50-80% compared to the corresponding solid cross-section of the attachment end 44.

Preferably, the ribs 40 have a variable rigidity which decreases moving from the dorsal side 36 to the ventral side 56; such variable rigidity may for example be achieved, as seen, by reducing the axial thickness of the ribs 40, that is the thickness measured in a direction parallel to the longitudinal direction X-X, moving from the attachment end 44 towards the free end 48.

A reduction of the radial thickness of the ribs 40 moving from the attachment end 44 towards the free end 48 may also be provided for, wherein the radial thickness is the thickness of the ribs 40 measured in relation to a cross-section plane perpendicular to the longitudinal direction X-X.

As may be seen from the description, the catheter according to the invention makes it possible to overcome the drawbacks presented in the prior art.

In particular, the inclination of the ribs permits a greater deformation and flattening of the profile of the catheter when this needs to be inserted in another catheter, such as for example, in the case of a guide catheter which needs to enter a feed catheter.

In addition, the inclination of the ribs permits a dilation when, inside the lumen of the catheter comprising such inclined rib conformation, another catheter or feeder of a slightly larger calibre compared to said inner lumen is inserted.

The catheter according to the invention may be devised so as to be applicable to different types of catheters and feeders.

Thereby making it possible to overcome the handicap of guide catheters or feeders which move along winding anatomies (see the aortic fork in the PTA/cross over stenting procedure) which, on account of the extensive bending which reduces the lumen and increases the friction, prevents the passage through it of catheters equal to the nominal lumen. Generally speaking today catheters having a diameter of at least one French (F) more than the catheter needed in rectilinear seats must be used. In these cases the ventral side must be placed on the outer side of the curvature axis rotating the catheter as needed.

In addition, the ventral area permits the association, if needed of an (outer) guide beside the guide catheter with a 'snake skeleton' core deforming it inwards in the ventral line of the catheter (where there is no core) maintaining an overall circumference enabling it to enter said feeder, (a feeder of a greater calibre is not needed).

In addition, the present invention does not require the ovalisation of the tip of a catheter created to permit the passage of the guide, allowing the tip of the catheter to retain a diameter identical to the rest of the catheter body for its entire length: this way important operating advantages are achieved for the passage of subsequent catheters and/or the overall diameter of said catheter may be reduced.

In addition, the present invention further makes it possible, using elastic covering material, to create feeders of variable diameter depending on the dilator used, the catheter being able to expand depending on the dilator used.

Flexible shape memory metal may be used or depending on use, expandable material capable of maintaining its shape may be used.

The functioning of the catheter according to the present invention derives from the co-operation of the core and the outer covering layer.

In fact, the core has the primary function of guaranteeing the characteristics of resistance upon advancement and rotation (pushability e torquability) of the catheter, that is to assure the necessary rigidity of the catheter so that it may be introduced and guided inside vessels or other instruments following the desired geometries.

In addition the core has the function of withstanding stresses and strains which the covering layer alone would not be able to withstand in the absence of armor, without incurring in plastic deformations or damage.

The area of the catheter body on the ventral side is at least partially without a core so as to permit a greater deformability of the catheter body to modify the through cross-section or lumen both in terms of compression and in terms of dilation.

A person skilled in the art may make modifications and variations to the catheters described above so as to satisfy contingent and specific requirements, while remaining within the sphere of protection of the invention as described and claimed herein.

The invention claimed is:

1. A catheter comprising a catheter body which extends from a proximal end to a distal end, along a longitudinal direction (X-X),
    the catheter body comprising a core embedded inside an outer covering layer, which is flexible being a hollow tubular body which defines a lumen,
    the core comprising a plurality of pairs of ribs which extend inside said outer covering layer, wherein said ribs extend from an attachment end, at which they connect to each other, to a free end, opposite the attachment end, wherein the line joining the attachment ends of the pairs of ribs defines a dorsal side of the catheter body,
    wherein the free ends of the ribs coupled in the same pairs are separate from each other, identifying at least one discontinuity of said ribs, said discontinuity being positioned on a ventral side, opposite said dorsal side,
    and wherein, a first plane (P) being defined perpendicular to a longitudinal element and passing through the attachment end of a rib, and a second plane (Q) being defined passing through the free end and through the attachment end of the same rib, said planes (P, Q) are inclined to each other so as to form an acute angle (A) on the side of the proximal end or of the distal end.

2. The catheter of claim 1, wherein the core of the catheter body comprises a longitudinal element from which the ribs coupled in pairs unravel on opposite sides to the longitudinal element, wherein the longitudinal element connects the attachment ends of the pairs of ribs to each other.

3. The catheter of claim 1, wherein said acute angle (A), formed between the first and second plane (P,Q), is from 10 to 70 degrees.

4. The catheter of claim 1, wherein said acute angle (A), formed between the first and second plane (P,Q), is from 40 to 60 degrees.

5. The catheter of claim 1, wherein the ribs, in relation to a projection plane (H) perpendicular to the longitudinal element and passing through a centreline (M) of the catheter body, have a rectilinear median line (S), said median line (S) being the place of the midpoints of the longitudinal thicknesses of the ribs, said longitudinal thicknesses being measured in relation to lines parallel to said longitudinal direction (X-X).

6. The catheter of claim 1, wherein the ribs, in relation to a projection plane (H) perpendicular to the longitudinal element and passing through a centreline (M) of the catheter body, have a curvilinear median line (S), said median line (S) being the place of the midpoints of the longitudinal thicknesses of the ribs, said longitudinal thicknesses being measured in relation to lines parallel to said longitudinal direction (X-X).

7. The catheter of claim 1, wherein the ribs are curvilinear and are oriented so as to present an intrados or concave portion, on the side of the proximal end, and an extrados, or convex portion, on the side of the distal end.

8. The catheter of claim 1, wherein the ribs present a first section which extends from the attachment end to an intermediate portion and which, in relation to a projection plane (H) perpendicular to the longitudinal element and passing through a centreline (M) of the catheter body, is inclined towards the distal end, and a second section which extends from the intermediate portion to the free end and which, in relation to said projection plane (H), is inclined towards the proximal end, so that the first and the second section have opposite inclinations to each other.

9. The catheter of claim 1, wherein at least an intermediate portion of the ribs extends from the first plane (P), passing through the attachment end and perpendicular to the longitudinal element, towards the distal end, and at least a second section of the rib, comprising said free end, extends from the first plane (P) towards the proximal end.

10. The catheter of claim 1, wherein the ribs are conformed and oriented in such a way that a radial plane (R), perpendicular to the longitudinal element, passing through free ends of a first pair of ribs, intercept at least partially an intermediate portion of a second pair of ribs, adjacent to the first pair of ribs, on the side of the proximal end.

11. The catheter of claim 1, wherein the ribs are tapered filaments.

12. The catheter of claim 1, wherein the ribs have a variable axial thickness, said thickness being measured parallel to said longitudinal direction.

13. The catheter of claim 12, wherein said axial thickness increases moving from the attachment end towards an intermediate portion and tapers moving from the intermediate portion towards the free end, the intermediate portion being comprised between the attachment end and the free end.

14. The catheter of claim 1, wherein each pair of ribs comprises ribs symmetrical to each other in relation to the longitudinal element.

15. The catheter of claim 1, wherein free ends of the same pair of ribs are separate from each other at a discontinuity having a curvilinear extension equal to at least 20% of the total perimeter of the catheter body, measured on a cross-section plane perpendicular to said longitudinal element.

16. The catheter of claim 1, wherein the discontinuity has a curvilinear extension of not more than 50% of the total perimeter of the catheter body, measured on a cross-section plane perpendicular to said longitudinal element.

17. The catheter of claim 1, wherein the ribs, at the attachment end, comprise at least one notch suitable for favouring the flexing of the ribs towards the proximal end, so as to keep a skirt of rib in one piece with the longitudinal element, positioned on the attachment end on the side of the proximal end and to have an opening positioned on the attachment end on the side of the distal end.

18. The catheter of claim 17, wherein said notch has a circular sector conformation.

19. The catheter of claim 17, wherein the opening has an extension of 50% to 80% of the cross-section of solid attachment, that is the notch consists of a removal of material of 50%-80% compared to the corresponding solid cross-section of the attachment end.

20. The catheter of claim 1 wherein the catheter body, in relation to a cross-section plane perpendicular to said longitudinal direction (X-X) has a hollow circular cross section.

21. The catheter of claim 1, wherein the catheter body, in relation to a cross-section plane perpendicular to said longitudinal direction (X-X) has a hollow elliptical/oval cross-section.

22. The catheter of claim 1, wherein a radial thickness of the ribs decreases moving from the attachment end towards the free end, wherein the radial thickness is the thickness of the ribs measured in relation to a cross-section plane perpendicular to the longitudinal direction (X-X).

* * * * *